(12) United States Patent  (10) Patent No.: US 8,175,714 B2
Greenberg et al.  (45) Date of Patent: May 8, 2012

(54) IMPLANTABLE RETINAL ELECTRODE ARRAY CONFIGURATION FOR MINIMAL RETINAL DAMAGE AND METHOD OF REDUCING RETINAL STRESS

(75) Inventors: Robert J. Greenberg, Los Angeles, CA (US); Alfred E. Mann, Beverly Hills, CA (US); James S. Little, Saugus, CA (US); Karl-Heinz Ihrig, Valencia, CA (US); Brian V. Mech, Valencia, CA (US); Neil H. Talbot, Montrose, CA (US); DaoMin Zhou, Saugus, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 13/044,825

(22) Filed: Mar. 10, 2011

(65) Prior Publication Data

US 2011/0166623 A1 Jul. 7, 2011

Related U.S. Application Data

(62) Division of application No. 11/728,144, filed on Mar. 23, 2007, now Pat. No. 8,060,211, which is a division of application No. 09/783,236, filed on Feb. 13, 2001, now Pat. No. 7,338,522.

(51) Int. Cl.
 *A61N 1/375* (2006.01)

(52) U.S. Cl. .......................................... 607/54; 607/53
(58) Field of Classification Search .................. 607/53, 607/54
 See application file for complete search history.

(56) References Cited

U.S. PATENT DOCUMENTS

| | | | |
|---|---|---|---|
| 4,573,481 A | 3/1986 | Bullara | |
| 4,969,468 A | 11/1990 | Byers et al. | |
| 5,024,223 A | 6/1991 | Chow | |
| 5,109,844 A | 5/1992 | de Juan, Jr. et al. | |
| 5,215,088 A | 6/1993 | Normann et al. | |
| 5,314,465 A * | 5/1994 | Maurer et al. | 607/138 |
| 5,324,322 A * | 6/1994 | Grill et al. | 607/118 |
| 5,476,494 A | 12/1995 | Edell et al. | |
| 5,810,725 A | 9/1998 | Sugihara et al. | |
| 5,935,155 A | 8/1999 | Humayun et al. | |
| 5,954,759 A * | 9/1999 | Swoyer et al. | 607/122 |
| 5,987,361 A | 11/1999 | Mortimer | |
| 6,038,480 A | 3/2000 | Hrdlicka et al. | |
| 6,393,327 B1 | 5/2002 | Scribner | |
| 6,400,989 B1 | 6/2002 | Eckmiller | |
| 6,458,157 B1 | 10/2002 | Suaning | |

* cited by examiner

*Primary Examiner* — Michael Kahelin
(74) *Attorney, Agent, or Firm* — Scott B. Dunbar; Gary Schnittgrund

(57) ABSTRACT

This invention is a retinal electrode array assembly and methods of using the same that facilitate surgical implant procedures by providing the operating surgeon with visual references and grasping means and with innovations that reduce actual and potential damage to the retina and the surrounding tissue.

15 Claims, 4 Drawing Sheets

IMPLANTABLE RETINAL ELECTRODE ARRAY CONFIGURATION FOR MINIMAL RETINAL DAMAGE AND METHOD OF REDUCING RETINAL STRESS

CROSS REFERENCE TO RELATED APPLICATION

This application is a divisional application of U.S. patent application Ser. No. 11/728,144, filed Mar. 23, 2007, now U.S. Pat. No. 8,060,211 entitled "IMPLANTABLE RETINAL ELECTRODE ARRAY CONFIGURATION FOR MINIMAL RETINAL DAMAGE AND METHOD OF REDUCING RETINAL STRESS", which is a divisional application of U.S. patent application Ser. No. 09/783,236, filed on Feb. 13, 2001, now U.S. Pat. No. 7,338,522 entitled "IMPLANTABLE RETINAL ELECTRODE ARRAY CONFIGURATION FOR MINIMAL RETINAL DAMAGE AND METHOD OF REDUCING RETINAL STRESS", which hereby incorporated by reference.

STATEMENT AS TO INVENTION RIGHTS UNDER FEDERALLY SPONSORED RESEARCH

This invention was made with government support under grant No. R24EY12893-01, awarded by the National Institutes of Health. The government has certain rights in the invention.

BACKGROUND OF THE INVENTION

1. Field of the Invention

This invention relates to a prosthetic medical ocular device and methods, and more particularly to an intraocular electrical retinal stimulation device that minimizes retinal damage during and after surgery, is easily manipulated by the surgeon performing the implant procedure, and to a method of reducing retinal stress.

2. Description of the Related Art Including Information Disclosed Under 37 CFR Secs. 1.97-1.99.

In 1755 LeRoy passed the discharge of a Leyden jar through the orbit of a man who was blind from cataract and the patient saw "flames passing rapidly downwards." Ever since, there has been a fascination with electrically elicited visual perception. The general concepts of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthesis devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across neuronal membranes, which can initiate neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface. This placement must be mechanically stable, minimize the distance between the device electrodes and the neurons, and avoid undue compression of the neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. Such a device increases the possibility of retinal trauma by the use of its "bed of nails" type electrodes that impinge directly on the retinal tissue.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina.

The retina is extraordinarily fragile. In particular, retinal neurons are extremely sensitive to pressure; they will die if even a modest intraocular pressure is maintained for a prolonged period of time. Glaucoma, which is one of the leading causes of blindness in the world, can result from a chronic increase of intraocular pressure of only 10 mm Hg. Furthermore, the retina, if it is perforated or pulled, will tend to separate from the underlying epithelium, which will eventually render it functionless. Thus attachment of a conventional prosthetic retinal electrode device carries with it the risk of damage to the retina, because of the pressure that such a device could exert on the retina.

Byers, et al. received U.S. Pat. No. 4,969,468 in 1990 which disclosed a "bed of nails" electrode array which in combination with processing circuitry amplifies and analyzes the signal received from the tissue and/or which generates signals which are sent to the target tissue. The penetrating electrodes are damaging to the delicate retinal tissue of a human eye and therefore are not applicable to enabling sight in the blind.

In 1992 U.S. Pat. No. 5,109,844 issued to de Juan et al. on a method of stimulating the retina to enable sight in the blind wherein a voltage stimulates electrodes that are in close proximity to the retinal ganglion cells. A planar ganglion cell-stimulating electrode is positioned on or above the retinal basement membrane to enable transmission of sight-creating stimuli to the retina. The electrode is a flat array containing 64-electrodes.

Norman, et al. received U.S. Pat. No. 5,215,088 in 1993 on a three-dimensional electrode device as a cortical implant for vision prosthesis. The device contains perhaps a hundred small pillars each of which penetrates the visual cortex in order to interface with neurons more effectively. The array is strong and rigid and may be made of glass and a semiconductor material.

U.S. Pat. No. 5,476,494, issued to Edell, et al. in 1995, describes a retinal array held gently against the retina by a cantilever, where the cantilever is is anchored some distance from the array. Thus the anchor point is removed from the area served by the array. This cantilever configuration introduces complexity and it is very difficult to control the restoring force of the cantilever due to varying eye sizes, which the instant invention avoids.

Sugihara, et al. received U.S. Pat. No. 5,810,725 in 1998 on a planar electrode to enable stimulation and recording of nerve cells. The electrode is made of a rigid glass substrate. The lead wires which contact the electrodes are indium tin oxide covered with a conducting metal and coated with platinum containing metal. The electrodes are indium tin oxide or a highly electrically conductive metal. Several lead-wire insulating materials are disclosed including resins.

U.S. Pat. No. 5,935,155, issued to Humayun, et al. in 1999, describes a visual prosthesis and method of using it. The Humayun patent includes a camera, signal processing electronics and a retinal electrode array. The retinal array is mounted inside the eye using tacks, magnets, or adhesives. Portions of the remaining parts may be mounted outside the eye. The Humayun patent describes attaching the array to the retina using retinal tacks and/or magnets. This patent does not address reduction of damage to the retina and surrounding tissue or problems caused by excessive pressure between the retinal electrode array and the retina.

Mortimer's U.S. Pat. No. 5,987,361 of 1999 disclosed a flexible metal foil structure containing a series of precisely positioned holes that in turn define electrodes for neural stimulation of nerves with cuff electrodes. Silicone rubber may be used as the polymeric base layer. This electrode is for going around nerve bundles and not for planar stimulation.

SUMMARY OF THE INVENTION

The apparatus of the instant invention is a retinal electrode array assembly in various embodiments with features that reduce irritation of the retina and the surrounding tissues during surgery and post-operatively and that facilitate installation by making the mounting aperture for placement of a surgical tack easy to locate and by providing a handle for use by the installing surgeon.

The retinal electrode array is made up of the electrode array body, which contains an array of electrodes and which is attached directly to the retina, feeder cable for transmitting electrical signals to the retina, and electronics which process the electrical signal before it is sent to the electrodes.

The electrode array body is made of soft silicone, having a hardness of about 50 on the Shore A scale as measured with a durometer, to assure intimate contact with the retina and to minimize stress concentrations in the retina. It has an over all oval shape avoiding stress concentrations in the retina by eliminating array corners. It is spherically curved so that it conforms readily to the curvature of the eye thereby minimizing contact stresses with the retina. It also has rounded edges to avoid contact stresses with the retina or tearing of the retina at the edge of the electrode array body. The edges may alternatively be progressively thinned (like a diver's flipper) to make a taper. The radius of curvature is reduced near the edge of the electrode array body, thus lifting the edge of the electrode array body away from the retina, thereby avoiding edge stress concentrations.

The electrode array body has at least one mounting aperture for attaching the electrode array to the retina by means of a mounting tack. The array also has a colored reinforcing ring that surrounds the mounting aperture in the array. The reinforcing ring is used for visually locating the mounting aperture during surgery and for structural support of a surgical tack.

In an alternate embodiment, the aperture and mounting tack are replaced with a ferromagnetic keeper that is placed in the electrode array body for mounting the electrode array body to the retina using magnetic attractive forces between the ferromagnetic keeper and a magnet.

The electrode array body contains an array of conductive electrodes to transmit electrical signals to the retina. One electrode may serve as a reference or ground potential return.

In order to eliminate stress in the retina from the mounting tack a strain relief internal tab is formed by placing a strain relief slot partially around the mounting aperture. The strain relief internal tab may be made of thinner silicone to minimize stress transfer from the mounting tack to the retina.

A grasping handle that is attached to the electrode array body is provided for use by the surgeon during placement of the electrode array body to avoid trauma to the eye during implantation. The feeder cable carries electrical signals between the electrodes and the electronics and contains a coil of electrical conductors to eliminate pulling of the array by the cable post-operatively due to mechanical or thermal stresses. The feeder cable is filled with soft silicone to stabilize the wire and to allow the coil to move somewhat within the cable.

OBJECTS OF THE INVENTION

It is the object of the invention to attach an electrode array body to the retina of an eye and enable blind people to see images.

It is the object of the invention to attach an electrode array body to the retina while avoiding or minimizing harmful stresses on the retina from the electrode array body.

It is the object of the invention to enable a surgeon to easily locate the mounting aperture for attachment of an electrode array body to the retina of an eye by a surgical tack.

It is the object of the invention to provide tabs for attachment of the electronics and feeder cable to the recipient of the retinal electrode array.

Other objects, advantages and novel features of the present invention will become apparent from the following detailed description of the invention when considered in conjunction with the accompanying drawing.

DETAILED DESCRIPTION OF THE PREFERRED EMBODIMENT

Figure 1:
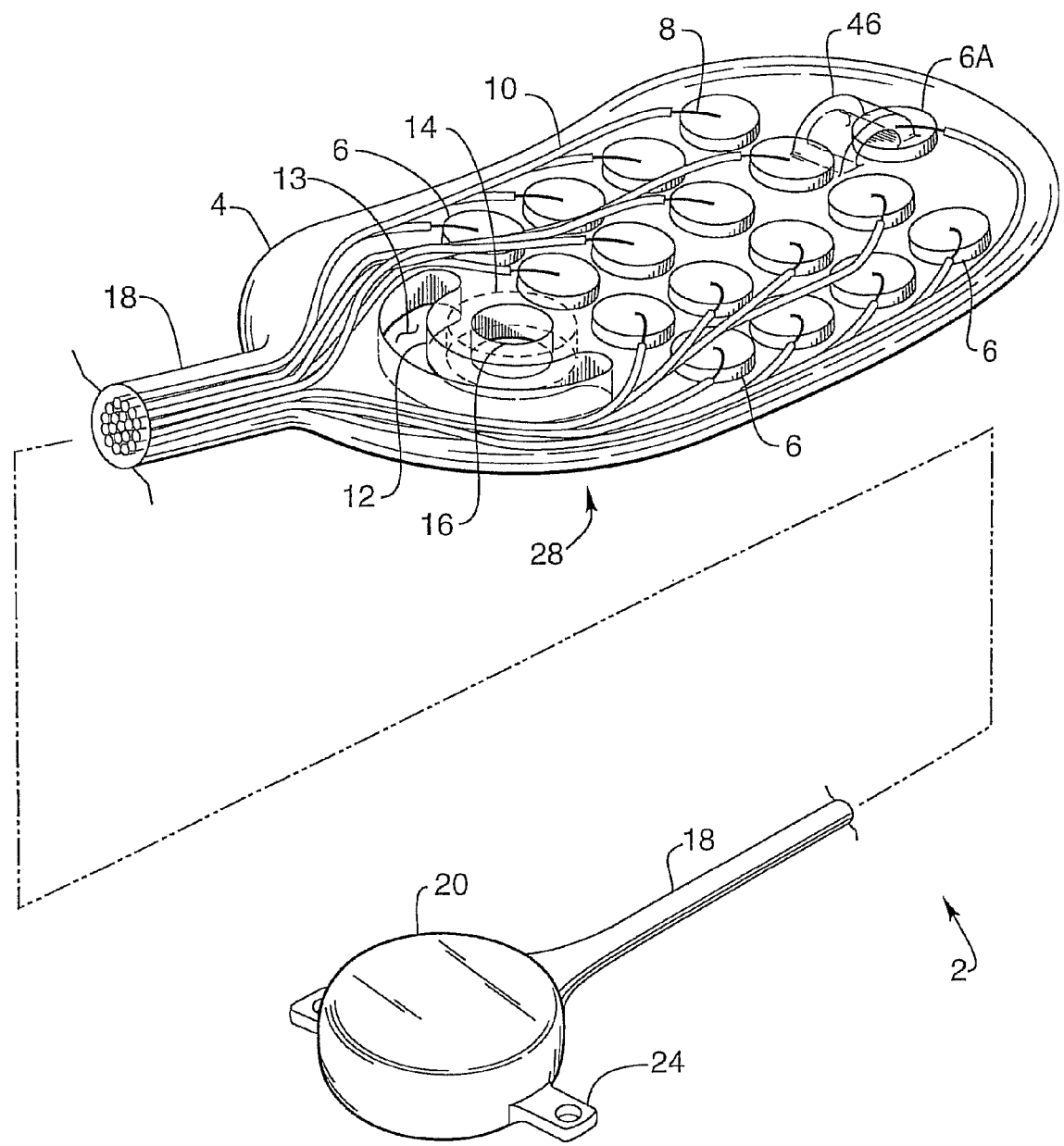
FIG. 1 illustrates a perspective view of the retinal electrode array assembly showing the electrodes and signal conductors as well as mounting aperture for tacking the assembly inside the eye, wherein both the array and its is associated electronics are located inside the eye.

FIG. 1 provides a perspective view of a preferred embodiment of the retinal electrode array, generally designated 2, comprising oval-shaped electrode array body 4, a plurality of electrodes 6 made of a conductive material, such as platinum or one of its alloys, but that can be made of any conductive biocompatible material such as iridium, iridium oxide or titanium nitride, and single reference electrode 6A made of the same material as electrode 6, wherein the electrodes are individually attached to separate conductors 8 made of a conductive material, such as platinum or one of its alloys, but which could be made of any biocompatible conductive material, that is enveloped within an insulating sheath 10, that is preferably silicone, that carries an electrical signal to each of the electrodes 6. "Oval-shaped" electrode array body means that the body may approximate either a square or a rectangle shape, but where the corners are rounded. The reference electrode 6A is not necessarily stimulated, but is attached to a conductor, as are electrodes 6. The electrodes could be used in another application as sensors to transmit electrical signals from a nerve. The electrodes 6 transmit an electrical signal to the eye while reference electrode 6A may be used as a ground, reference, or control voltage.

Electrode array body 4 is made of a soft material that is compatible with the body. In a preferred embodiment array body 4 is made of silicone having a hardness of about 50 or less on the Shore A scale as measured with a durometer. In an alternate embodiment the hardness is about 25 or less on the Shore A scale as measured with a durometer. It is a substantial goal to have electrode array body 4 in intimate contact with the retina of the eye.

Strain relief internal tab 12, defined by a strain relief slot 13 that passes through the array body 4, contains a mounting aperture 16 for fixation of the electrode array body 4 to the retina of the eye by use of a surgical tack, although alternate means of attachment such as glue or magnets may be used. Reinforcing ring 14 is colored and opaque to facilitate locating mounting aperture 16 during surgery and may be made of tougher material, such as high toughness silicone, than the body of the electrode array body to guard against tearing.

Signal conductors 8 are located in an insulated flexible feeder cable 18 carrying electrical impulses from the electronics 20 to the electrodes 6, although the electrodes can be sensors that carry a signal back to the electronics. Signal conductors 8 can be wires, as shown, or in an alternative embodiment, a thin electrically conductive film, such as platinum, deposited by sputtering or an alternative thin film deposition method. In a preferred embodiment, the entire retinal electrode array 2 including the feeder cable 18 and electronics 6 are all implanted inside the eye. Electronics 20 may be fixated inside the eye to the sclera by sutures or staples that pass through fixation tabs 24. The conductors are covered with silicone insulation.

Grasping handle 46 is located on the surface of electrode array body 4 to enable its placement by a surgeon using forceps or by placing a surgical tool into the hole formed by grasping handle 46. Grasping handle 46 avoids damage to the electrode body that might be caused by the surgeon grasping the electrode body directly. Grasping handle 46 also minimizes trauma and stress-related damage to the eye during surgical implantation by providing the surgeon a convenient method of manipulating electrode array body 4. Grasping handle 46 is made of silicone having a hardness of about 50 on the Shore A scale as measured with a durometer. A preferred embodiment of the electrode array body 4 is made of a very soft silicone having hardness of 50 or less on the Shore A scale as measured with a durometer. The reinforcing ring 14 is made of opaque silicone having a hardness of 50 on the Shore A scale as measured with a durometer.

Figure 2:
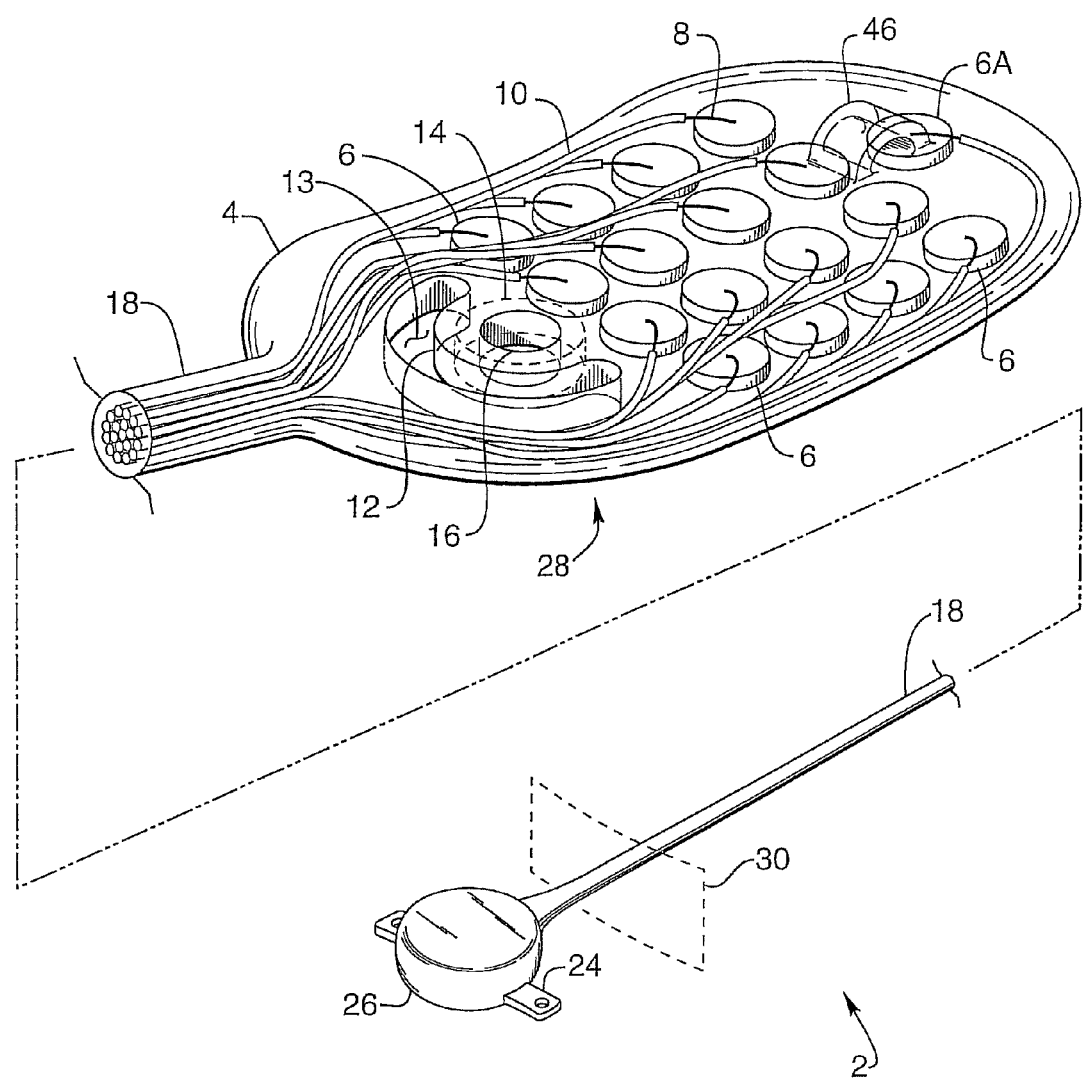
FIG. 2 illustrates a perspective view of the retinal electrode array assembly showing the electrodes and signal conductors as well as mounting aperture for tacking the assembly inside the eye, wherein the associated electronics are located outside the eye.

FIG. 2 provides a perspective view of the retinal electrode array assembly 2 wherein the electrode array body 4 is implanted inside the eye and the electronics 20 are placed outside the eye with the feeder cable 18 passing through sclera 30. In this embodiment, electronics 38 are attached by fixation tabs 24 outside the eye to sclera 30.

Figure 3:
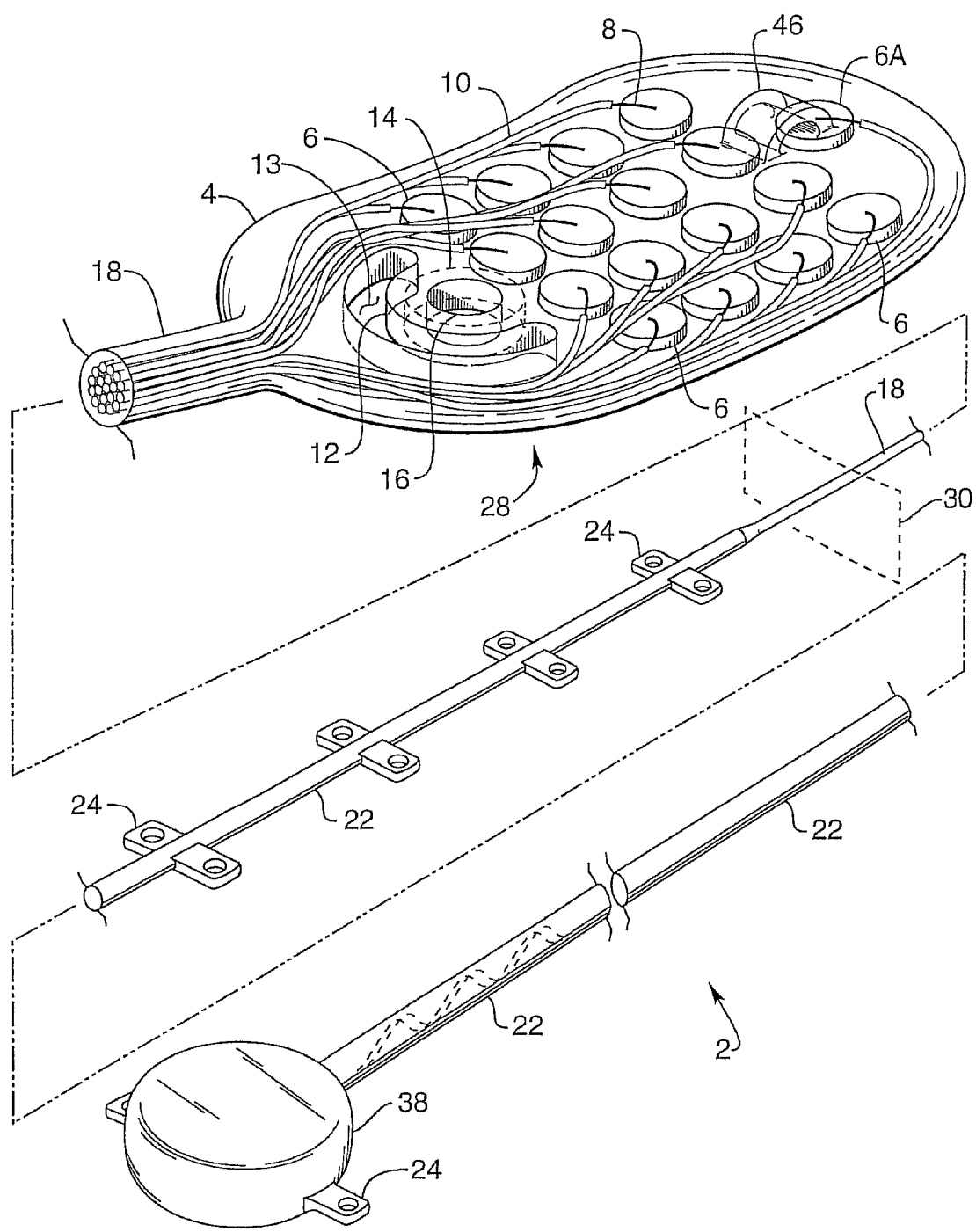
FIG. 3 illustrates a perspective view of the retinal electrode array assembly wherein the array is installed inside the eye and the associated electronics are installed outside the eye at some distance from the sclera wherein the feeder cable contains both a coiled cable leading between the electronics and the sclera and a series of fixation tabs along the feeder cable for securing the feeder cable by suture.

FIG. 3 provides a perspective view of retinal electrode array 2 wherein electrode array body 4 is implanted on the retina inside the eye and electronics 38 are placed outside the eye some distance from sclera 30 wherein feeder cable 18 contains sheathed conductors 10 as silicone-filled coiled cable 22 for stress relief and flexibility between electronics 38 and electrode array body 4. Feeder cable 18 passes through sclera 30 and contains a series of fixation tabs 24 outside the eye and along feeder cable 18 for fixating cable 18 to sclera 30 or elsewhere on the recipient subject.

Figure 4:
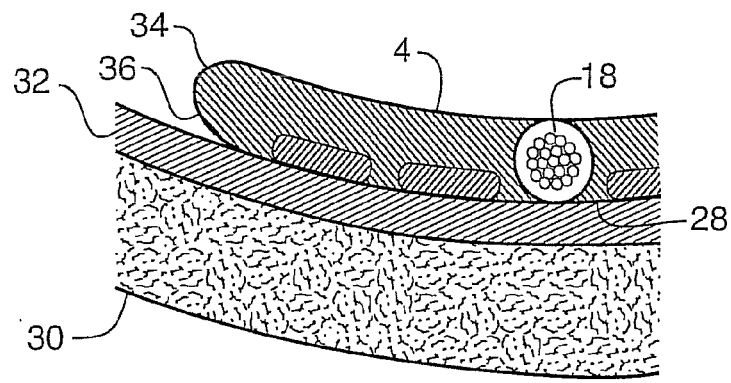
FIG. 4 depicts a cross-sectional view of the retinal electrode array, the sclera, the retina and the retinal electrode array showing the electrodes in contact with the retina.

FIG. 4 provides a cross-sectional view of electrode array body 4 in intimate contact with retina 32. The surface of electrode array body 4 in contact with retina 32 is a curved surface 28 substantially conforming to the spherical curvature of retina 32 to minimize stress concentrations therein. Further, the decreasing radius of spherical curvature of electrode array body 4 near its edge forms edge relief 36 that causes the edges of array body 4 to lift off the surface of retina 32 eliminating stress concentrations. The edge of electrode array body 4 has a rounded edge 34 eliminating stress and cutting of retina 32. The axis of feeder cable 18 is at right angles to the plane of this cross-sectional view. Feeder cable 18 is covered with silicone.

Figure 5:
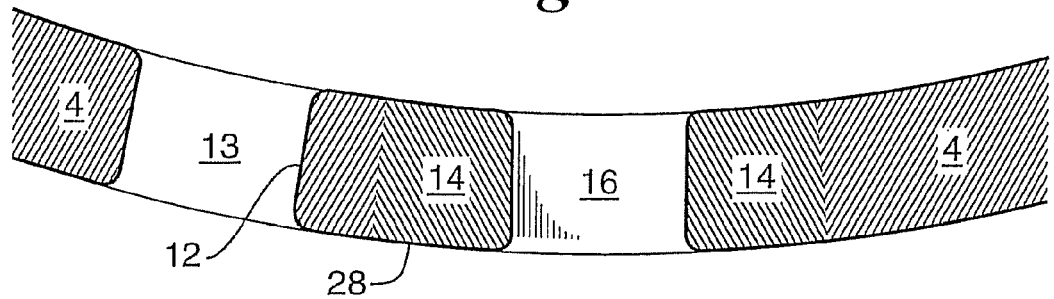
FIG. 5 depicts a cross-sectional view of the retinal electrode array showing a strain relief slot, strain relief internal tab and a mounting aperture through a reinforcing ring for a mounting tack to hold the array in position.

FIG. 5 provides a cross-sectional view of electrode array body 4 showing spherically curved surface 28, strain relief slot 13 and mounting aperture 16 through which a tack passes to hold array body 4 in intimate contact with the eye. Mounting aperture 16 is located in the center of reinforcing ring 14 that is opaque and colored differently from the remainder of array body 4, making mounting aperture 16 visible to the surgeon. Reinforcing ring 14 is made of a strong material such as tough silicone, which also resists tearing during and after surgery. Strain relief slot 13 forms strain relief internal tab 12 in which reinforcing ring 14 is located. Stresses that would otherwise arise in the eye from tacking array body 4 to the eye through mounting aperture 16 are relieved by virtue of the tack being located on strain relief internal tab 12.

Figure 6:
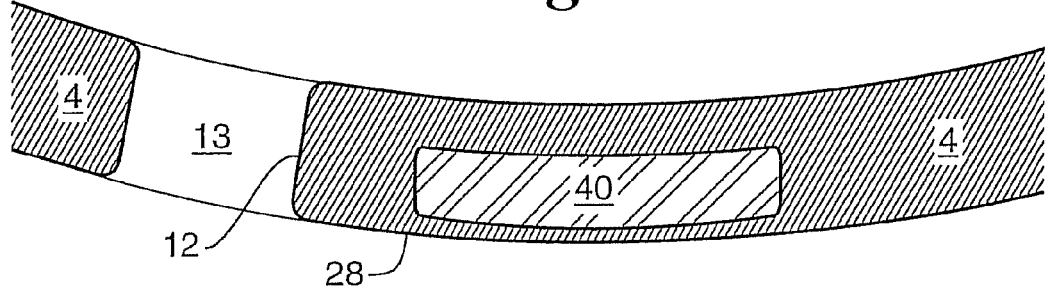
FIG. 6 illustrates a cross-sectional view of the retinal electrode array showing a strain relief slot and a ferromagnetic keeper to hold the array in position.

FIG. 6 provides a cross-sectional view of a preferred embodiment of electrode array body 4 showing ferromagnetic keeper 40 that holds electrode array body 4 in position against the retina by virtue of an attractive force between keeper 40 and a magnet located on and attached to the eye.

Figure 7:
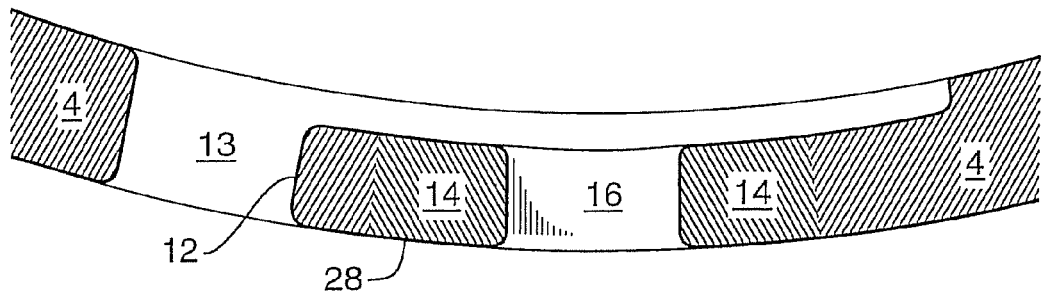
FIG. 7 illustrates a cross-sectional view of the retinal electrode array showing a strain relief slot and a mounting aperture through a reinforcing ring for a mounting tack to hold the array in position, wherein the strain relief internal tab containing the mounting aperture is thinner than the rest of the array.

FIG. 7 is a cross-sectional view of the electrode array body 4 wherein internal tab 12 is thinner than the rest of electrode array body 4, making this section more flexible and less likely to transmit attachment induced stresses to the retina. This embodiment allows greater pressure between array body 4 and the retina at the point of attachment, and a lesser pressure at other locations on array body 4, thus reducing stress concentrations and irritation and damage to the retina.

Obviously, many modifications and variations of the present invention are possible in light of the above teachings. It is therefore to be understood that, within the scope of the appended claims, the invention may be practiced otherwise than as specifically described.

What we claim is:

1. A retinal prosthesis comprising:
    an electronics package adapted to be implanted external to an eye having a sclera and a retina and distant from the sclera, further adapted to process electrical signals before being sent to an electrode array body, while at the distant location;
    said electrode array body comprised of a plurality of electrodes adapted to intimately contact the retina to provide vision-inducing stimulation to the retina; and
    a feeder cable, comprised of sections, including a plurality of conductors configured to couple said electronics package to said electrode array body when said electrode array body is in contact with the retina and the electronics package is distant from the sclera, said feeder cable configured to pass through the sclera and not through the retina.

2. The retinal prosthesis according to claim 1, wherein said plurality of conductors are coiled within said feeder cable.

3. The retinal prosthesis according to claim 2, wherein said section of said feeder cable, suitable to be placed within an eye, has straight conductors.

4. The retinal prosthesis according to claim 1, wherein the feeder cable is silicone filled.

5. The retinal prosthesis according to claim 4, wherein said silicone has hardness of about 50 or less on the Shore A scale as measured with a durometer.

6. The retinal prosthesis according to claim 1, wherein said plurality of conductors are individually sheathed.

7. The retinal prosthesis according to claim 1, wherein said plurality of conductors are wires.

8. The retinal prosthesis according to claim 1, wherein said plurality of conductors are electrically conductive film.

9. The retinal prosthesis according to claim 1, further comprising one or more fixation tabs on the feeder cable.

10. The retinal prosthesis according to claim 9, wherein said one or more fixation tabs are comprised of silicone.

11. The retinal prosthesis according to claim 1, wherein said plurality of conductors are platinum.

12. The retinal prosthesis according to claim 1, wherein said feeder cable is covered with silicone.

13. The retinal prosthesis according to claim 12, wherein said silicone has hardness of about 50 or less on the Shore A scale as measured with a durometer.

14. The retinal prosthesis according to claim 1, further comprising a grasping handle attached to the feeder cable for holding with a surgical instrument during implantation.

15. The retinal prosthesis according to claim 1, wherein said electronics package is hermetically sealed.

* * * * *